(12) United States Patent
Marom et al.

(10) Patent No.: US 8,981,095 B2
(45) Date of Patent: Mar. 17, 2015

(54) INTERMEDIATE COMPOUNDS AND PROCESS FOR THE PREPARATION OF LURASIDONE AND SALTS THEREOF

(75) Inventors: Ehud Marom, Kfar Saba (IL); Michael Mizhiritskii, Rehovot (IL); Susanna Tchilibon, Jerusalem (IL); Shai Rubnov, Tel Aviv (IL)

(73) Assignee: Mapi Pharma Ltd., Ness Ziona (IL)

( * ) Notice: Subject to any disclaimer, the term of this patent is extended or adjusted under 35 U.S.C. 154(b) by 0 days.

(21) Appl. No.: 14/235,593

(22) PCT Filed: Jun. 13, 2012

(86) PCT No.: PCT/IL2012/050208
§ 371 (c)(1),
(2), (4) Date: Jan. 28, 2014

(87) PCT Pub. No.: WO2013/014665
PCT Pub. Date: Jan. 31, 2013

(65) Prior Publication Data
US 2014/0179922 A1 Jun. 26, 2014

Related U.S. Application Data

(60) Provisional application No. 61/512,424, filed on Jul. 28, 2011.

(51) Int. Cl.
| | | |
|---|---|---|
| C07D 417/12 | (2006.01) | |
| C07D 417/14 | (2006.01) | |
| C07D 209/44 | (2006.01) | |
| C07D 209/48 | (2006.01) | |
| C07C 309/04 | (2006.01) | |
| C07D 275/04 | (2006.01) | |
| C07D 209/72 | (2006.01) | |

(52) U.S. Cl.
CPC ............ *C07D 417/14* (2013.01); *C07D 209/44* (2013.01); *C07C 309/04* (2013.01); *C07D 275/04* (2013.01); *C07D 417/12* (2013.01); *C07D 209/72* (2013.01); *C07D 209/48* (2013.01)
USPC .......................................................... 544/368

(58) Field of Classification Search
USPC .......................................................... 544/368
See application file for complete search history.

(56) References Cited

U.S. PATENT DOCUMENTS

| | | |
|---|---|---|
| 4,140,692 A | 2/1979 | Fleig et al. |
| 4,411,901 A | 10/1983 | Temple, Jr. et al. |
| 4,590,196 A | 5/1986 | Smith et al. |
| 4,745,117 A | 5/1988 | Ishizumi et al. |
| 5,532,372 A | 7/1996 | Saji et al. |
| 5,780,632 A | 7/1998 | Saji et al. |
| 7,605,260 B2 | 10/2009 | Kakiya et al. |
| 7,829,569 B2 | 11/2010 | Liao et al. |
| 2004/0166155 A1 | 8/2004 | Dobetti et al. |
| 2006/0089502 A1 | 4/2006 | Venkataraman et al. |
| 2007/0116729 A1 | 5/2007 | Palepu |
| 2007/0218012 A1 | 9/2007 | Bittorf et al. |
| 2007/0259857 A1 | 11/2007 | Gray |
| 2009/0054455 A1 | 2/2009 | Devarakonda et al. |
| 2009/0143404 A1 | 6/2009 | Fujihara |
| 2010/0093875 A1 | 4/2010 | Matsui et al. |
| 2010/0119612 A1 | 5/2010 | Friesen et al. |

FOREIGN PATENT DOCUMENTS

| | | |
|---|---|---|
| CN | 101362751 A | 2/2009 |
| EP | 0398425 A1 | 11/1990 |
| EP | 0398426 A1 | 11/1990 |
| EP | 0464846 A1 | 1/1992 |
| EP | 0741129 A2 | 11/1996 |
| JP | 04013663 A | 1/1992 |
| JP | 2004224764 A | 8/2004 |
| JP | 2006282527 A | 10/2006 |
| WO | 93/16073 A1 | 8/1993 |
| WO | 94/18196 A1 | 8/1994 |

OTHER PUBLICATIONS

Arrizabalaga et al., (1984) Intramolecular influence of a carboxylic function on platinum blue synthesis. A systematic study of complexes originating from acid amides. J Am Chem Soc 106(17): 4814-4818.

Böshagen and Geiger (1977) Synthese von 3-Aminoisothiazolen. Justus Liebigs Ann Chem 1977(1): 20-26.

Moriconi and Crowford (1968) Reaction of chlorosulfonyl isocyanate with bridge bi- and tricyclic olefins. J Org Chem 33 (1): 370-378.

Vicini et al., (2007) Benzo[d]isothiazol-3-yl-benzamidines: a Class of Protective Agents on Culture of Human Cartilage and Chondrocytes Stimulated by IL-1β. ChemMedChem 2(1): 113-119.

Walinsky et al., (1999) New Disulfide Route to 3-(1-Piperazinyl)-1,2-benzisothiazole. Nucleus for Atypical Antipsychotic Drugs. Org Proc Res Dev 3(2): 126-130.

Yevich et al., (1986) Synthesis and biological evaluation of 1-(1,2-benzisothiazol-3-yl)- and (1,2-benzisoxazol-3-yl) piperazine derivatives as potential antipsychotic agents. J Med Chem 29(3): 359-369.

Zhiqin et al., (2008) 3-Amino-benzo[d]isoxazoles as Novel Multitargeted Inhibitors of Receptor Tyrosine Kinases. J Med Chem 51(5): 1231-1241.

*Primary Examiner* — Bruck Kifle
(74) *Attorney, Agent, or Firm* — Rothwell, Figg, Ernst & Manbeck, P.C.

(57) ABSTRACT

The present invention relates to a process for the preparation of Lurasidone or a pharmaceutically acceptable salt thereof, a compound useful for the treatment of schizophrenia and bipolar disorder. The present invention further relates to processes for the preparation of Lurasidone intermediates, and to certain novel intermediates obtained by such processes.

13 Claims, No Drawings

INTERMEDIATE COMPOUNDS AND PROCESS FOR THE PREPARATION OF LURASIDONE AND SALTS THEREOF

CROSS REFERENCE TO RELATED APPLICATIONS

This application is a 35 U.S.C. §371 National Phase Entry Application from PCT/IL2012/050208, filed Jun. 13, 2012, and designating the United States, which claims priority to U.S. Patent Application No. 61/512,424 filed Jul. 28, 2011, which are incorporated herein in their entireties.

FIELD OF THE INVENTION

The present invention relates to a process for the preparation of (3aR,4S,7R,7aS)-2-[((1R,2R)-2-{[4-(1,2-benzisothiazol-3-yl)-piperazin-1-yl]methyl}cyclohexyl)methyl] hexahydro-1H-4,7-methanisoindol-1,3-dione (Lurasidone) and salts thereof, a compound useful for the treatment of schizophrenia and bipolar disorder. The present invention further relates to processes for the preparation of Lurasidone intermediates, and to certain novel intermediates obtained by such processes.

BACKGROUND OF THE INVENTION

Lurasidone hydrochloride (SM-13,496) is an atypical antipsychotic marketed by Dainippon Sumitomo Pharma (DSP) and its subsidiary Sunovion Pharmaceuticals Inc. under the trade name LATUDA for the treatment of schizophrenia.

The preparation of Lurasidone (1) [JP2004224764 (SUMITOMO PHARMA, 2004)] is performed by consecutive additions of building blocks (2), (3) and (5) (Scheme 1). In a first step, 1,2-(1R,2R) bis(methanesulfonyloxymethyl)cyclohexane (2) reacts with 1-(1,2-benzisothiazol-3-yl)piperazine (3) to form the spirocyclic compound (4). Then, compound (4) reacts with bicyclo[2.2.1]heptane-2-exo-3-exo-dicarboximide (5) and forms Lurasidone (1).

Scheme 1

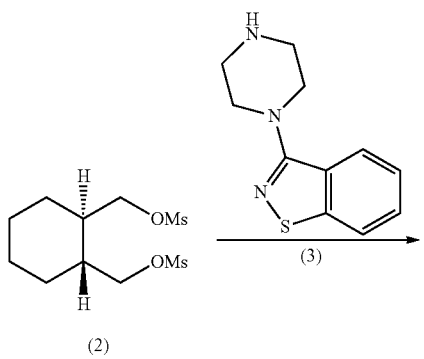

(2)

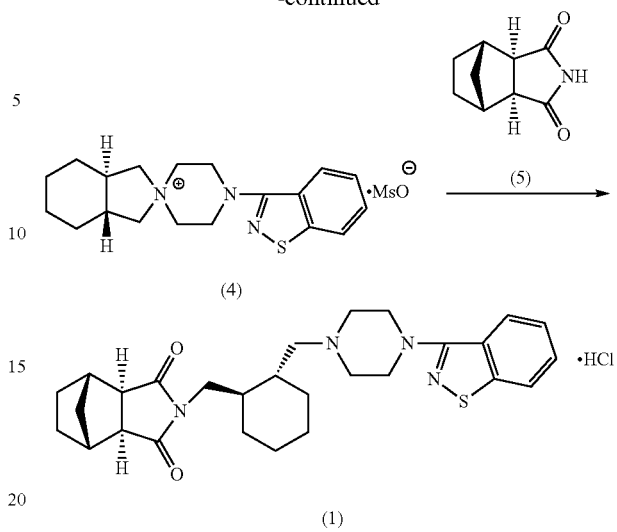

(4)

(1)

3-Chloro-1,2-benzisothiazole and its synthetic precursor 1,2-benzisothiazole-3(2H)-one are used in the manufacturing process of building block (3). These intermediates are considered strong dermal, ocular, and nasal irritants which require process containment and special handling.

In addition, the processes for the preparation of Lurasidone and its intermediates use hazardous materials and involve sophisticated separation techniques which make them commercially less viable. Therefore, there exists a need to develop a process for obtaining Lurasodine in an enantiomerically pure form which is cost effective, uses available reagents, is scalable with ease and industrially feasible.

SUMMARY OF THE INVENTION

The present invention provides a process for the preparation of Lurasidone, or a pharmaceutically acceptable salt thereof, especially the hydrochloride salt, on a manufacturing scale from a compound of formula (A).

According to a first aspect, the present invention provides a process for the preparation of a compound of formula (1'), or a salt thereof, comprising the following steps:

a) reacting a compound of formula A' with a compound of formula B' to form a compound of formula C':

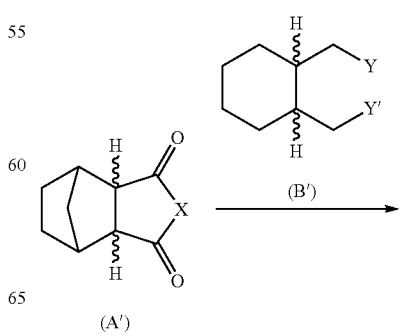

(A')

-continued

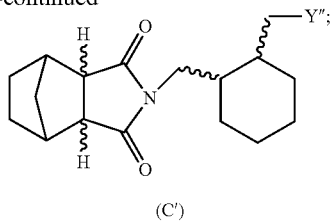

(C')

and
b) reacting the compound of formula C' with a compound of formula D to form a compound of formula 1'

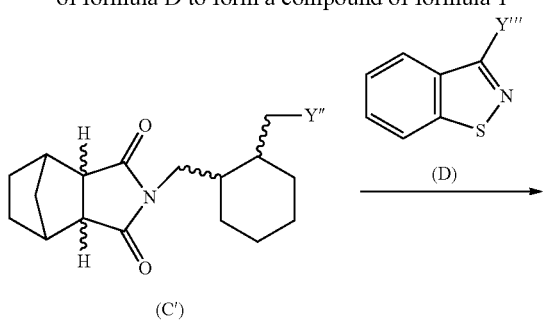

wherein
X is selected from O and NH;
Y and Y' are independently selected from OH, OSO$_2$R, NH$_2$ and Hal, or Y and Y' together are N(CH$_2$CH$_2$Z)$_2$ wherein Z is selected from OH, OSO$_2$R, and Hal;
Y" is selected from OH, OSO$_2$R, NH$_2$, Hal, and N(CH$_2$CH$_2$Z)$_2$ wherein Z is as defined above;
Y''' is selected from NH$_2$ and piperazinyl;
Hal is selected from Cl, Br, and I; and
R is selected from substituted or unsubstituted alkyl and aryl.

According to a second aspect, the present invention provides a process for the preparation of Lurasidone, a compound of formula (1), or a salt thereof, comprising the following steps:
a) reacting a compound of formula A with a compound of formula B to form a compound of formula C:

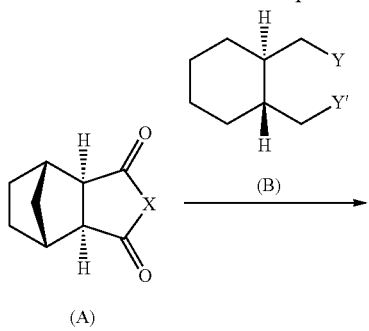

-continued

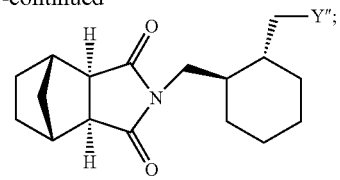

(C)

and
b) reacting a compound of formula C with a compound of formula D to form Lurasidone (1):

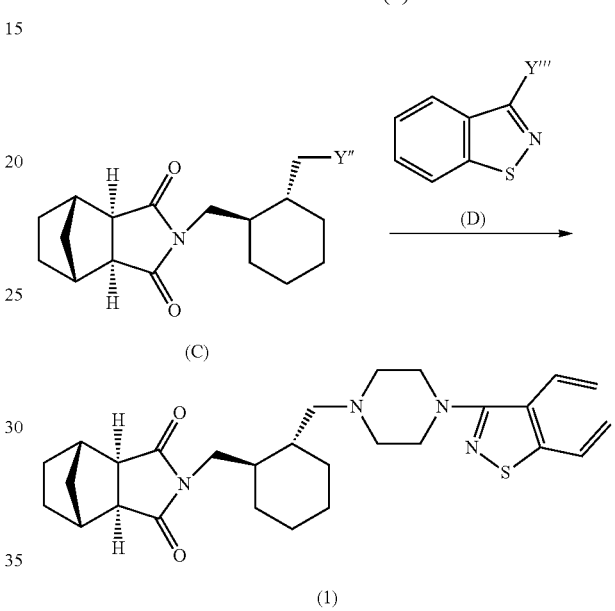

wherein
X is selected from O and NH;
Y and Y' are independently selected from OH, OSO$_2$R, NH$_2$, and Hal, or Y and Y' together are N(CH$_2$CH$_2$Z)$_2$ wherein Z is selected from OH, OSO$_2$R, and Hal;
Y" is selected from OH, OSO$_2$R, NH$_2$, Hal, and N(CH$_2$CH$_2$Z)$_2$ wherein Z is as defined above;
Y''' is selected from NH$_2$ and piperazinyl;
Hal is selected from Cl, Br, and I; and
R is selected from substituted or unsubstituted alkyl and aryl.

In one embodiment, the process further comprises the step of converting the compound of formula (1) or (1') to its pharmaceutically acceptable salt. Preferably, the compound is Lurasidone or a salt thereof, especially Lurasidone HCl.

In some embodiments of step (a), X is O; Y and Y' are independently selected from OH and NH$_2$; and Y" is OH. In one particular embodiment, step (a) comprises reacting a compound of formula (9) with a compound of formula (6) to generate a compound of formula (13) (Scheme 3).

In some embodiments of step (a), X is NH; Y and Y' together are N(CH$_2$CH$_2$OH)$_2$ and Y" is N(CH$_2$CH$_2$OH)$_2$. In one particular embodiment, step (a) comprises reacting a compound of formula (7) with a compound of formula (5) to generate a compound of formula (10) (Scheme 4).

In some embodiments of step (b), Y" is N(CH$_2$CH$_2$OSO$_2$R)$_2$ or N(CH$_2$CH$_2$Hal)$_2$ and Y''' is NH$_2$. In one particular embodiment, step (b) comprises reacting a compound of formula (12) with a compound of formula (16) to generate Lurasidone (1) (Scheme 6).

In another particular embodiment, step (b) comprises reacting a compound of formula (11) with a compound of formula (16) to generate Lurasidone (1) (Scheme 6).

In other embodiments of step (b), Y" is OSO₂R; and Y'" is piperazinyl. In one particular embodiment, step (b) comprises reacting a compound of formula (14) with a compound of formula (17) to generate Lurasidone (1) (Scheme 6).

The present invention further relates to certain intermediates formed in the process of the present invention. Thus, in one aspect, the present invention provides a compound of formula B' having the following structure:

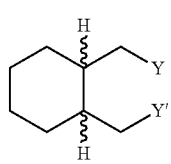

(B')

wherein Y and Y' together form a zwitterion N⊕(CH₂CH₂Z)₂Z'⊖; Z is selected from OH, OSO₂R, and Hal; Z' is selected from OSO₂R, and Hal; Hal is selected from Cl, Br, and I; and R is selected from substituted or unsubstituted alkyl and aryl.

In some embodiments, the compound of formula B' is in a racemic mixture. In alternative embodiments, the compound of formula B' is in an enantiomerically pure form, for example a compound of formula B:

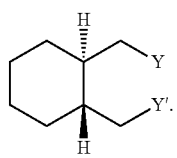

(B)

It is understood that, in compound (B) or (B'), when Y and Y' together form a group of the formula, N(CH₂CH₂Z)₂, the resultant compound is a zwitterion of the formula:

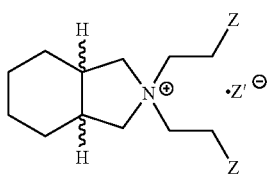

wherein Z' is a counter-ion, such as (but not limited to) OSO₂R and Hal; wherein R is an unsubstituted or substituted alkyl or aryl and Hal is halogen.

In some embodiments, the compound of formula B is in an enantiomerically pure form represented by the following structure:

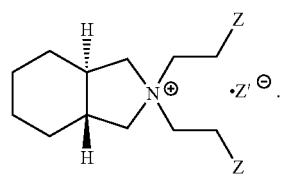

In yet another aspect, the present invention provides a compound of formula C' having the following structure:

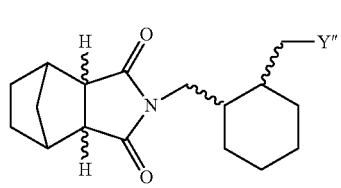

(C')

wherein Y" is selected from NH₂, N(CH₂CH₂OH)₂, N(CH₂CH₂Hal)₂, N(CH₂CH₂OSO₂R)₂, OH, OSO₂R, and Hal; Hal is selected from Cl, Br, and I; and R is selected from substituted or unsubstituted alkyl and aryl.

In various embodiments, the compound of formula C' is in a racemic mixture. In alternative embodiments, the compound of formula C' is in an enantiomerically pure form. In particular embodiments, the compound of formula C' is in enantiomerically pure form represented by the following structure:

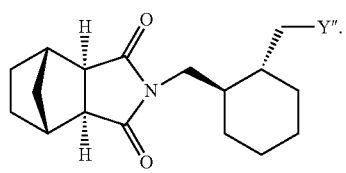

(C)

The present invention further relates to novel intermediates of formula (D), and processes for their preparation. Thus, according to another aspect, the present invention provides a method for the preparation of 3-(1-piperazinyl)-1,2-benzisothiazole of the formula,

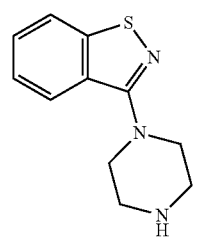 [SMILES: c1ccc2c(N3CCNCC3)nsc2c1]

The method comprising the following steps:
a) sulfonation of 1,2-benzisothiazol-3(2H)-one of the formula

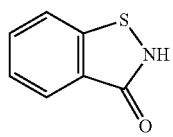

using a sulfonating reagent;

b) reaction of the sulfonated compound with a compound of the general formula

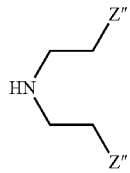

so as to obtain a compound of the general formula

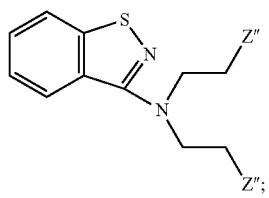

wherein Z" is selected from OH, OSO$_2$R, and Hal; Hal is selected from Cl, Br, and I;

and R is selected from substituted or unsubstituted alkyl and aryl; and c) reacting the obtained compound with ammonia or equivalent thereof so as to obtain 3-(1-piperazinyl)-1,2-benzisothiazole.

In one embodiment, the sulfonating reagent is selected from an alkylsulfonyl chloride, an arylsulfonyl chloride and anhydride derivatives thereof. In certain embodiments, the alkylsulfonyl chloride is methanesulfonyl chloride. In other embodiments, the arylsulfonyl chloride is p-toluenesulfonyl chloride.

In another embodiment, the ammonia equivalent is ammonium carbonate or monoprotected ammonia derivatives such as Boc-NH$_2$, Bzl-NH$_2$, and Ac—NH$_2$. Each possibility represents a separate embodiment of the invention.

In an additional aspect, the present invention provides a compound having the following structure:

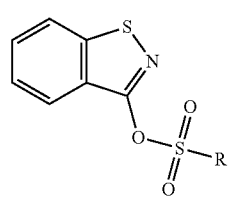

wherein R is selected from substituted or unsubstituted alkyl and aryl.

In a further aspect, the present invention provides a compound having the following structure:

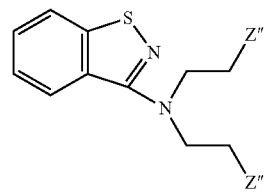

wherein Z" is selected from OH, OSO$_2$R, and Hal; Hal is selected from Cl, Br, and I;

and R is selected from substituted or unsubstituted alkyl and aryl.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The applicants have unexpectedly found a new process, by which Lurasidone or salts thereof may be prepared on a manufacturing scale from the compound of formula (A) by several steps (scheme 2). Thus, in some embodiments, the present invention provides a process for preparing Lurasidone, or salts thereof, which proceeds as shown in Scheme 2 by consecutive addition of four building blocks A to D:

Scheme 2

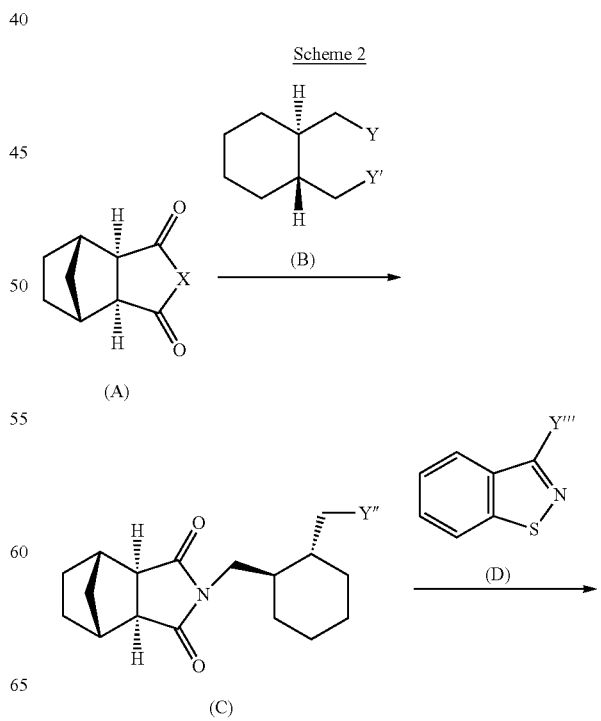

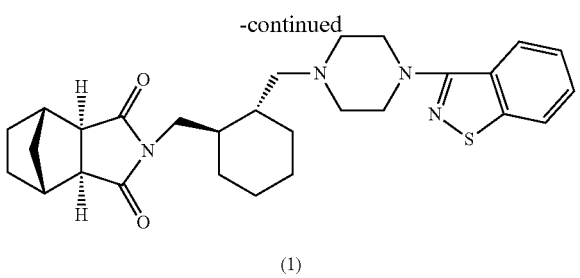

In another embodiment, the present invention provides a process for preparing a compound of formula (1'), or salts thereof, which proceeds as shown in Scheme 2A by consecutive addition of four building blocks:

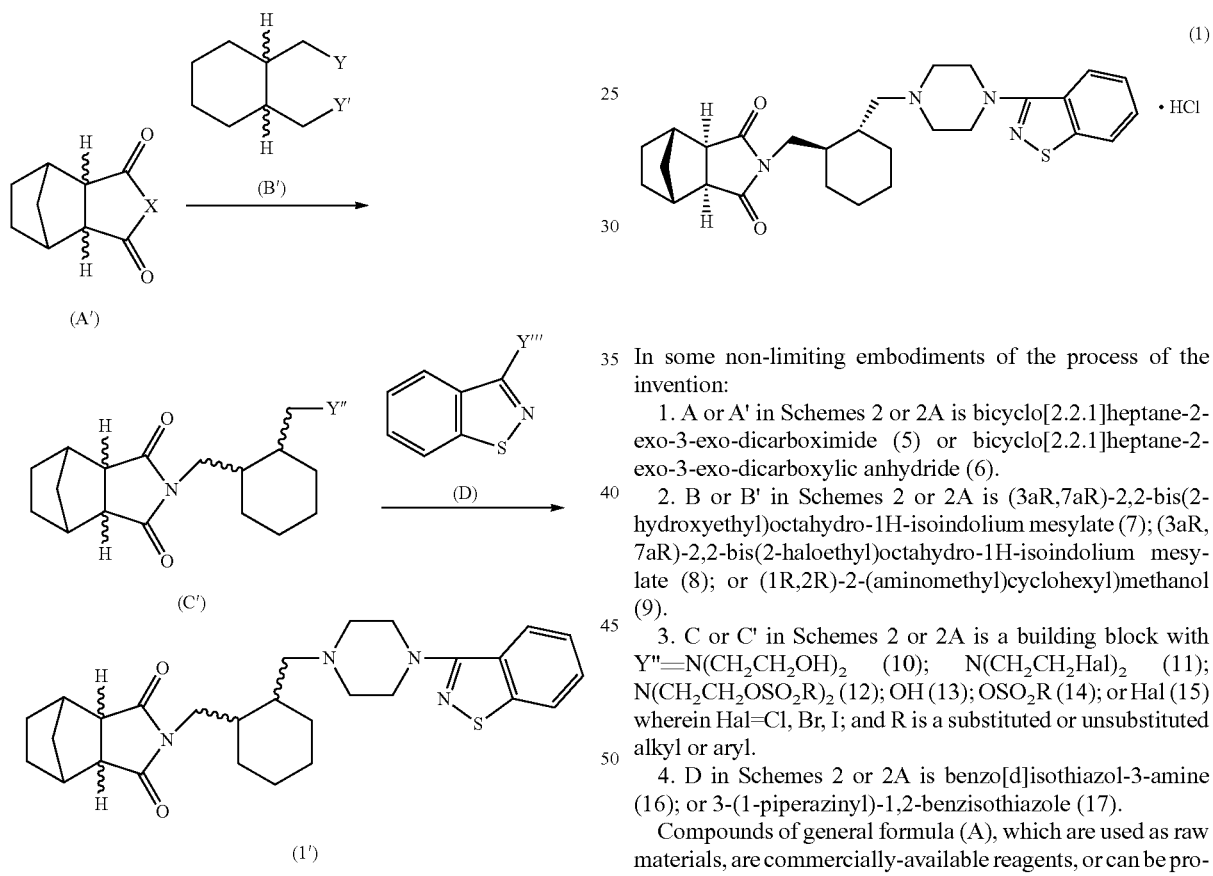

wherein, in schemes 2A or 2B:

X is selected from O and NH;

Y and Y' are independently selected from OH, $OSO_2R$, $NH_2$, and Hal, or Y and Y' together are $N(CH_2CH_2Z)_2$ wherein Z is selected from OH, $OSO_2R$, and Hal;

Y'' is selected from OH, $OSO_2R$, $NH_2$, Hal, and $N(CH_2CH_2Z)_2$ wherein Z is as defined above;

Y''' is selected from $NH_2$ and piperazinyl;

Hal is selected from Cl, Br, and I; and

R is selected from substituted or unsubstituted alkyl and aryl.

Optionally, the process further comprises the step of converting the compound of formula (1') into its pharmaceutically acceptable salt. The term "pharmaceutically acceptable salt" refers to an acid addition salt wherein the acid is an organic or inorganic acid. In one preferred embodiment, the salt is a HCl salt. In other embodiments, the acid addition salts include, but are not limited to, salts derived from hydrobromic, hydrofluoric, trifluoroacetic, sulfuric, phosphoric, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids. Each possibility represents a separate embodiment of the present invention.

For example, the process of the invention may further comprise the step of converting Lurasidone of formula (1) to its pharmaceutically acceptable salt, e.g., the HCl salt:

In some non-limiting embodiments of the process of the invention:

1. A or A' in Schemes 2 or 2A is bicyclo[2.2.1]heptane-2-exo-3-exo-dicarboximide (5) or bicyclo[2.2.1]heptane-2-exo-3-exo-dicarboxylic anhydride (6).

2. B or B' in Schemes 2 or 2A is (3aR,7aR)-2,2-bis(2-hydroxyethyl)octahydro-1H-isoindolium mesylate (7); (3aR,7aR)-2,2-bis(2-haloethyl)octahydro-1H-isoindolium mesylate (8); or (1R,2R)-2-(aminomethyl)cyclohexyl)methanol (9).

3. C or C' in Schemes 2 or 2A is a building block with Y'''=$N(CH_2CH_2OH)_2$ (10); $N(CH_2CH_2Hal)_2$ (11); $N(CH_2CH_2OSO_2R)_2$ (12); OH (13); $OSO_2R$ (14); or Hal (15) wherein Hal=Cl, Br, I; and R is a substituted or unsubstituted alkyl or aryl.

4. D in Schemes 2 or 2A is benzo[d]isothiazol-3-amine (16); or 3-(1-piperazinyl)-1,2-benzisothiazole (17).

Compounds of general formula (A), which are used as raw materials, are commercially-available reagents, or can be produced by well-known methods as described in e.g. JP4013663; CN101362751; and Moriconi, E. J and Crowford W. C. *J. Org. Chem.*, 1968, Vol. 33, No. 1, p. 370-8, the contents of each of which are incorporated by reference herein.

Step (a)—Preparation of Intermediate C

The present invention provides a process for preparing a Lurasidone intermediate of formula C, involving a reaction of a compound of formula A with a compound of formula B. It is understood by a person of skill in the art that corresponding process for preparing the racemate C' can be conducted by reacting a compound of formula A' with a compound of formula B'.

In one embodiment, the preparation of the abovementioned intermediate may be carried out by reacting bicyclo[2.2.1]heptane-2-exo-3-exo-dicarboxylic anhydride (6) (compound A) with (1R,2R)-2-(aminomethyl)cyclohexyl) methanol (9) (compound B) in the presence of a base in a suitable organic solvent, preferably with heating, as shown in Scheme 3.

Scheme 3

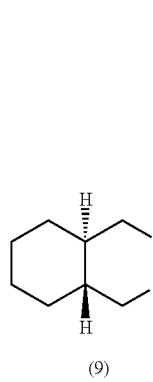
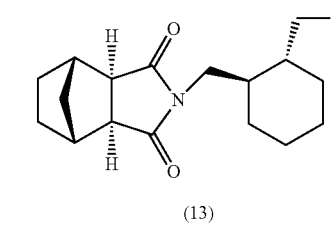

In some embodiments, the reaction is accelerated in the presence of a base and/or by azeotropic removal of water. Preferably, the reaction is carried out at a temperature between about 10° C. and 150° C., more preferably at about 100-125° C. The reaction is conducted in any suitable solvent, which may for example be selected from the group consisting of C6 to C14 aromatic hydrocarbons, C2 to C10 linear or branched alcohols and diols, C2 to C7 esters, C4 to C7 ethers, C1 to C5 carboxylic acid amides, e.g. DMF or suitable mixtures of these solvents. Each possibility represents a separate embodiment of the invention. Exemplary solvents include, but are not limited to, aromatic hydrocarbons, such as benzene, toluene, xylene, and chlorobenzene. Each possibility represents a separate embodiment of the invention.

Suitable bases for conducting this step include, but are not limited to, tertiary amines such as triethylamine, diisopropylethylamine, N-methylmorpholine, pyridine, lutidine, DBU, DBN and the like. Each possibility represents a separate embodiment of the invention.

The obtained compound (13) may be used without further purification in the next step or it may be purified by any suitable technique, for example, by crystallization or through column chromatography.

Alternatively, in another non-limiting embodiment, a Lurasidone intermediate of formula C can be prepared by reacting bicyclo[2.2.1]heptane-2-exo-3-exo-dicarboximide (5) with (3aR,7aR)-2,2-bis(2-hydroxyethyl)octahydro-1H-isoindolium mesylate (7):

Scheme 4

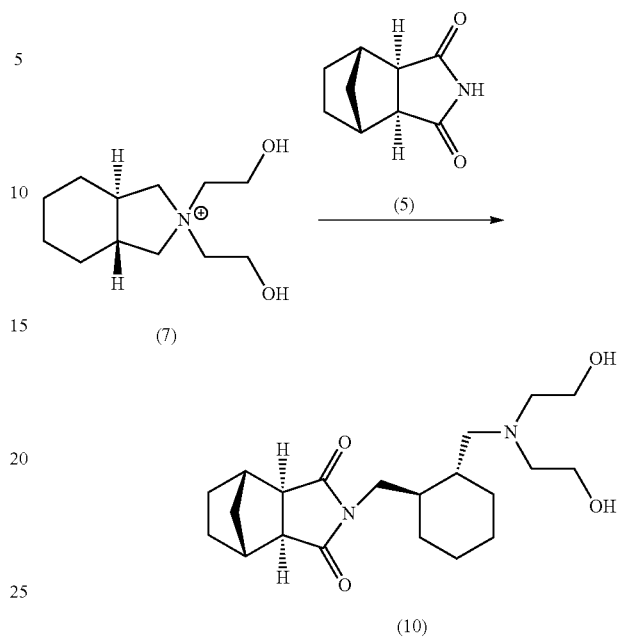

Alternatively, (3aR,7aR)-2,2-bis(2-haloethyl)octahydro-1H-isoindolium mesylate (8) can be used in place of compound (7).

Alternatively, in another non-limiting embodiment, a Lurasidone intermediate of formula C can be prepared by reacting compound of formula (2) with bicyclo[2.2.1]heptane-2-exo-3-exo-dicarboximide (5):

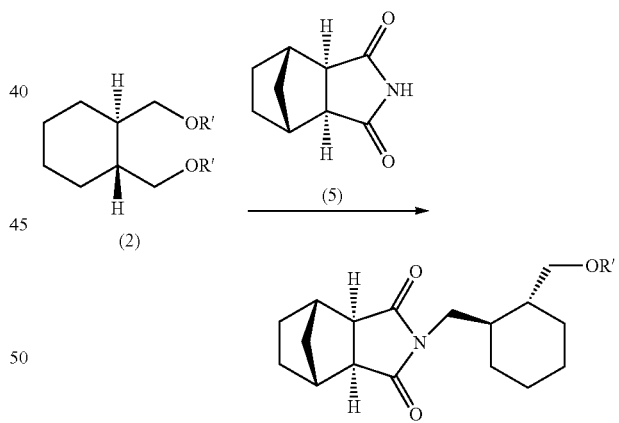

wherein R' is SO₂R and R is selected from substituted or unsubstituted alkyl and aryl.

Each of the aforementioned reactions can be carried out in a suitable organic solvent at a temperature between 10° C. and 120° C., more preferably at a temperature between about 50 and 70° C. It is understood that the reaction can also be conducted with the racemic analogs of compounds (7) and (5), to generate a racemic analog of the compound of formula (10).

Suitable organic solvents for this step include, but are not limited to, halogenated hydrocarbons, aromatic hydrocarbons, esters, ethers, and mixture thereof, preferably acetonitrile, toluene, acetone, or THF. Each possibility represents a separate embodiment of the invention.

Suitable bases for this step include, but are not limited to, alkali metal and alkaline earth carbonates, and hydroxides, for example potassium bicarbonate, sodium bicarbonate, potassium carbonate, sodium carbonate, sodium hydroxide, potassium hydroxide, calcium hydroxide, and the like; tertiary amines such as triethylamine, tributylamine, diisopropylethylamine, N-methylmorpholine, pyridine, lutidine, DBN, DBU and the like; and basic resins. Each possibility represents a separate embodiment of the invention. Bases to which preference is currently given are alkali metal carbonates, such as potassium carbonate and sodium carbonate.

The reaction may be facilitated by an addition of phase-transfer catalysts, crown ethers or by using micro wave irradiation.

Compound C can be isolated from the reaction mixture by conventional means, for example, by extraction to obtain two phases, separating the organic layer, and evaporating the organic layer to obtain a residue. Evaporation can be carried out at an elevated temperature of about 45° C. to about 60° C. and/or a pressure of less than about one atmosphere. The resulting crude product can be further purified by any suitable technique, for example, by crystallization or through column chromatography.

Step (b)—Preparation of Lurasidone (1)

The present invention comprises a process for preparing Lurasidone, or salts thereof (e.g., the HCl salt) involving a reaction of building block (C) with a compound of formula (D).

Building block (C) is preferably used in its activated form, which is prepared by a transformation of the OH group of compound C into alkyl- or arylsulfonates, or halogens, such as chloro-, bromo- or iodo-derivatives, or into an N(CH$_2$CH$_2$Z)$_2$ containing derivative, as illustrated in scheme 5.

It is understood that the process shown in Scheme 5 can also be conducted with racemic reactants instead of the optically active compounds shown in this scheme. Alkyl- or arylsulfonation of building block (C), for example of compounds (10) and (13), may be carried out in the presence of a hydrogen chloride scavenger in a suitable organic solvent. Suitable hydrogen chloride scavengers include, but are not limited to, alkali metal and alkaline earth carbonates or hydroxides, for example potassium bicarbonate, sodium bicarbonate, potassium carbonate, sodium carbonate, sodium hydroxide, potassium hydroxide, calcium hydroxide, alkali metal and alkaline earth hydrides, such as sodium hydride, potassium hydride, and the like; and organic amines such as triethylamine, diisopropylethylamine, N-methylmorpholine, pyridine, lutidine and the like; ammonia and basic resins, and the like. Each possibility represents a separate embodiment of the invention. Bases to which current preference is given are organic amines.

Any commercial grade of alkyl- or arylsulfonyl chlorides can be employed in the process of the invention. While other sulfonating reagents, such as methanesulfonyl anhydride (mesyl anhydride), p-toluenesulfonyl anhydride (tosyl anhydride), trifluoromethanesulfonyl anhydride (triflic anhydride) and alkyl- or arylsulfonyl bromides, may also be employed in the process of this invention, methanesulfonyl chloride is preferred due its substantially lower cost.

Suitable amides and tertiary amines with high boiling temperatures may be used in the present invention as catalysts. Examples of amides or amines that can be used in the present invention include, but are not limited to, pyrrolidinones, ureas, acetamides, phosphoramides, such as N-methyl-2-pyrrolidinone (hereafter referred to as NMP), 1,1,3,3-tetramethylurea, dimethylacetamide (DMAC), hexamethylphosphoramide (HMPA), and dimethylformamide (DMF). Each Scheme 5

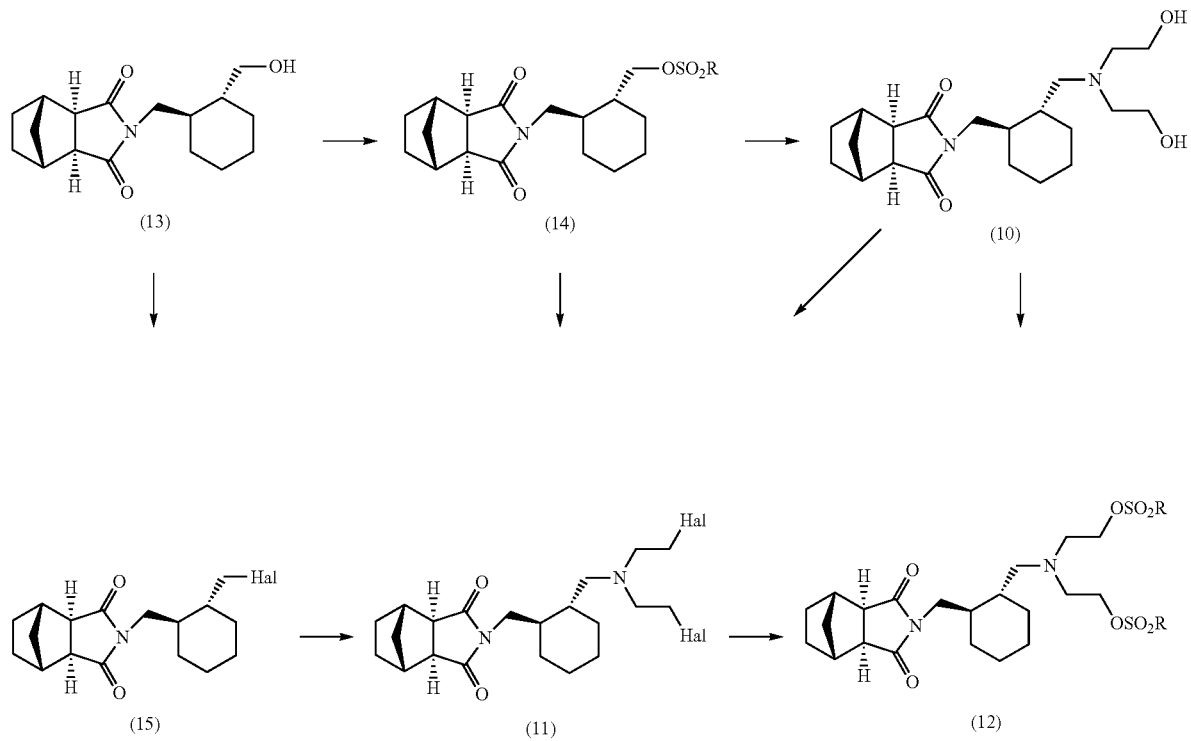

possibility represents a separate embodiment of the invention. The preferred amides can be used in catalytic amounts as additives to the solvents or as solvents per-se.

Suitable solvents that can be used in the present invention are those that allow for the formation of a miscible mixture with building block (C) at an elevated temperature. Examples of solvents that may be used in the present invention include, but are not limited to, aromatic and aliphatic hydrocarbons, chlorinated solvents, ethers, DMF, NMP, DMSO, acetonitrile, esters, and suitable mixtures of these solvents. Each possibility represents a separate embodiment of the invention.

The methanesulfonation is preferably carried out in a temperature range of about 10° C. to 80° C. Temperatures between about 20° C. to 45° C. are preferred because these provide useful reaction rates while minimizing the decomposition of the methanesulfonyl chloride. The reaction time for the methanesulfonation is generally from about 15 minutes to 48 hours, preferably from about 30 minutes to 18 hours, more preferably from 1 to 5 hours.

The transformation of alcohols into the corresponding alkyl halides can be achieved by methods well known in art (R. Larock, C., *Comprehensive Organic Transformations: A Guide to Functional Group Preparations*, 2nd Ed., Wiley-VCH, New York, 1999, p. 689), the contents of which are incorporated by reference herein. Most of these methods utilize reagents such as thionyl chloride, oxalyl chloride, phosphorus halides, phenylmethyleniminium, benzoxazolium, Vilsmeier-Haack, and Viehe salts; (chloro-phenylthiomethylene)dimethylammonium chloride; triarylphosphines such as triphenylphosphine or trialkylphosphine such as tributylphosphine in combination with carbon tetrahalides, bromine, bromotrichloromethane, $Cl_3CCCl_3$, $Cl_3CCOCCl_3$, $Cl_3CCN$, $Cl_3CCONH_2$, N-halo succinimides, N-halo saccharins, 2,3-dichloro-5,6-dicyanobenzoquinone; reagents based on a polymer-supported triphenyl phosphine or a filterable phosphine source such as 1,2-bis(diphenylphosphino)ethane, halide-based ionic liquids. The preference is given to cheap and available reagents such as thionyl chloride, oxalyl chloride, phosphorus halides or 2,4,6-trichloro[1,3,5]triazine.

In another embodiment, the present invention further relates to a process for preparing Lurasidone of formula (1), involving a reaction of an activated compound of formula (C) with benzisothiazole derivative (D), the latter is exemplified in scheme 6 as compounds (16) and (17):

Scheme 6

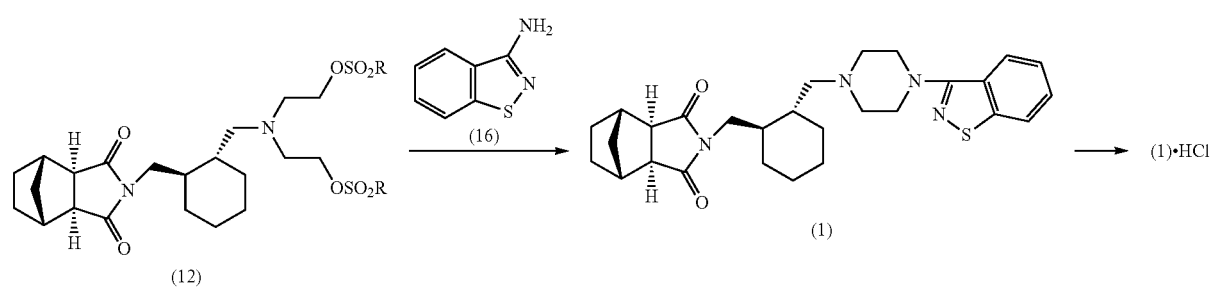

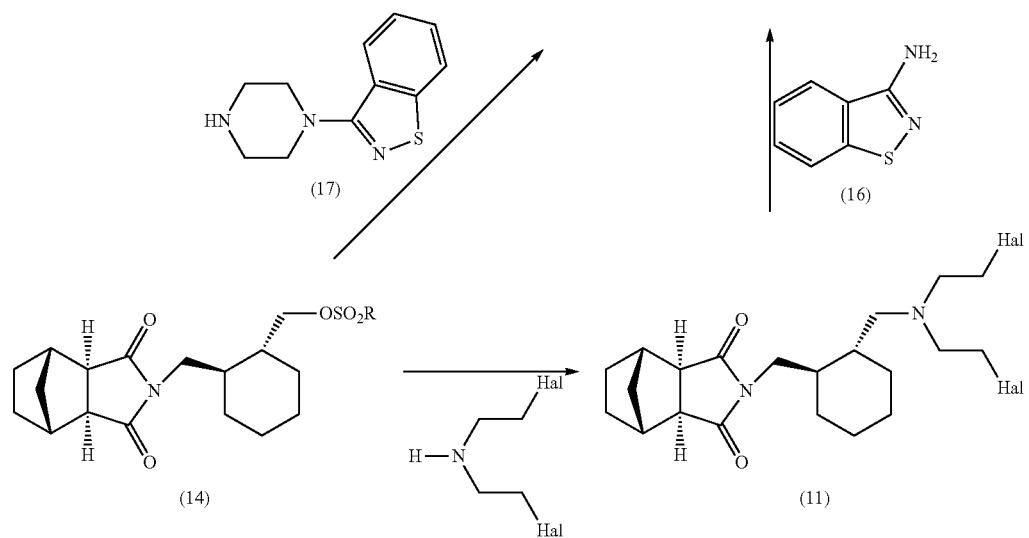

wherein R is selected from substituted or unsubstituted alkyl and aryl, and Hal is halogen. Lurasidone (1) is then optionally converted to its salt form, preferably the HCl salt.

In one particular embodiment, the process is illustrated in Scheme 6A:

amine (16) (Liebigs *Ann. Chem.* 1977, 20-26; *Chem. Med. Chem* 2007, 2, 113-119; *J. Med. Chem.* 2008, 51, 1231-1241; and U.S. Pat. No. 4,140,692); 3-(1-piperazinyl)-1,2-benzisothiazole (17) (U.S. Pat. No. 4,411,901; U.S. Pat. No. 4,745,117; *J. Med. Chem.* 1986, 29, 359-369; U.S. Pat. No.

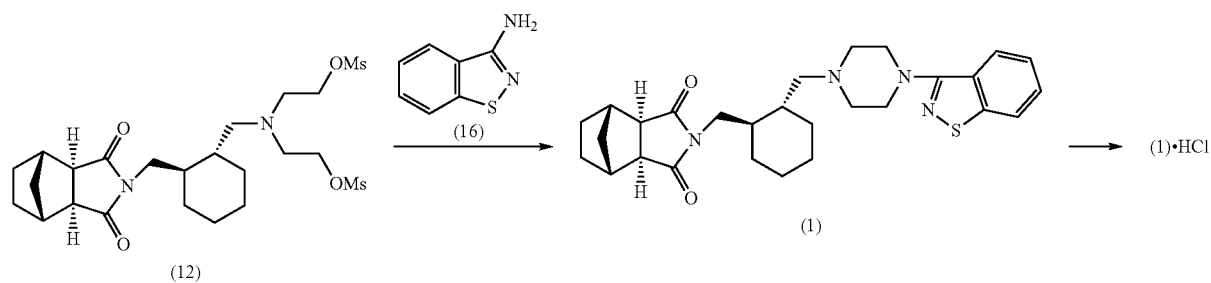

Scheme 6A

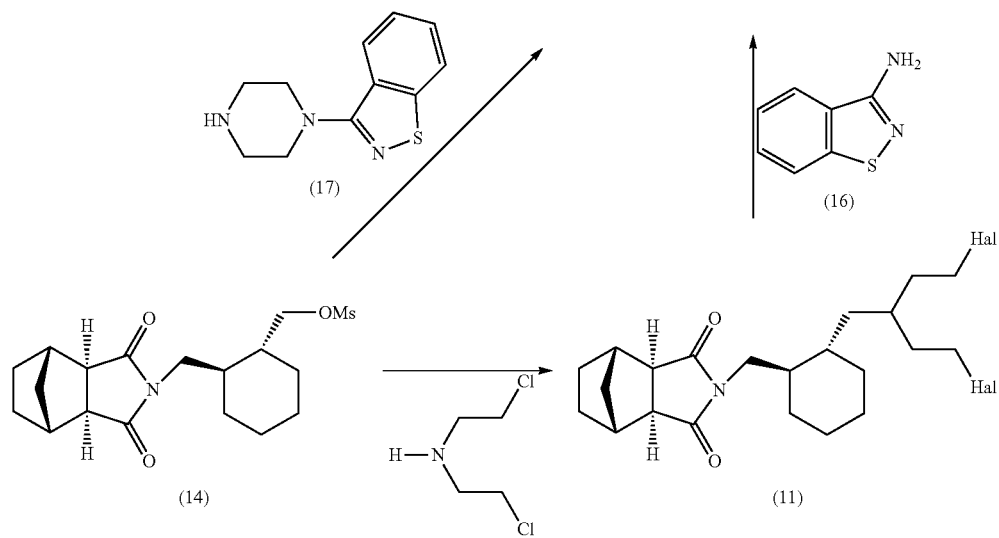

It is understood that the processes shown in Schemes 6 or 6A can also be conducted with racemic reactants instead of the optically active compounds shown in these schemes.

Benzisothiazole derivatives of general formula (D), which are used here as raw materials are commercially-available reagents or can be produced by well-known methods described in the following references: benzo[d]isothiazol-3-

4,590,196; US 2006/089502; EP0741129; and *Organic Process Research & Development* 1999, 3, 126-130).

In another aspect of the present invention, 3-(1-piperazinyl)-1,2-benzisothiazole (17) can be prepared from commercially available 1,2-benzisothiazol-3(2H)-one, according to the following scheme 7:

Scheme 7

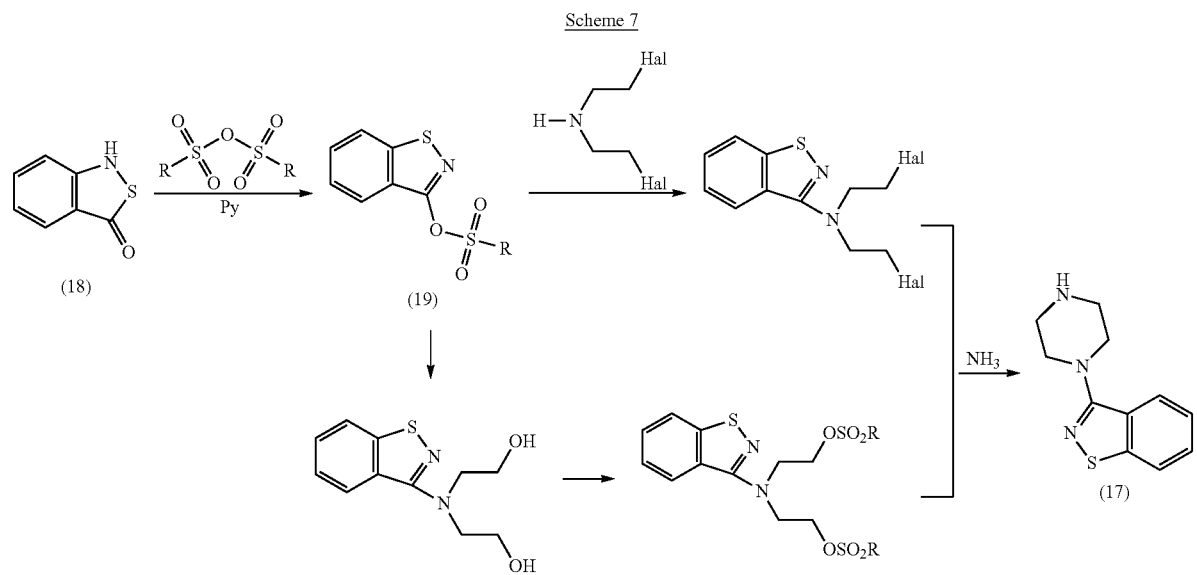

wherein R is selected from substituted or unsubstituted alkyl and aryl, and Hal is halogen. In one particular embodiment, the process is illustrated in Scheme 7A:

Scheme 7A

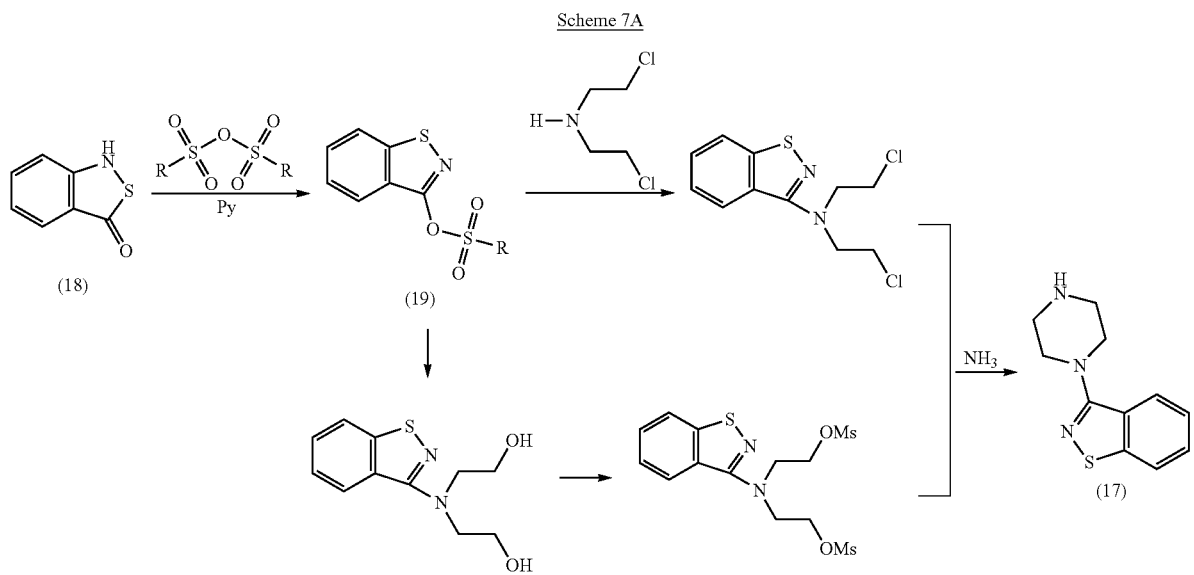

wherein R is an unsubstituted alkyl or aryl.

Alternatively, in Schemes 7 and 7A, a sulfonyl halide (e.g., sulfonyl chloride) can be used instead of the sulfonyl anhydride in the conversion of compound (18) to compound (19).

It is understood that the processes shown in Schemes 7 or 7A can also be conducted with racemic reactants instead of the optically active compounds shown in these schemes.

Alkyl- or arylsulfonation of 1,2-benzisothiazol-3(2H)-one (18) using sulfonyl chloride or anhydride yields the corresponding sulfonyl ester (19), which can be directly transformed to 3-(1-piperazinyl)-1,2-benzisothiazole (17) by a reaction with piperazine. However, this direct reaction calls for an excess of piperazine (10-20 mol of pipearazine for each mol of 1,2-benzisothiazol-3(2H)-one) and provides only moderate yield of the desired compound (17) (40-55%). Due to these limitations, an alternate synthetic pathway as described above is selected, which requires an additional step, but provides a better overall yield (75-85%).

The reaction of the activated compound of formula (C) with the benzisothiazole derivative (D) may be carried out in the presence of a base (inorganic or organic) in a suitable organic solvent at elevated temperatures. Temperatures between about 40° C. to 80° C. are preferred.

The product may be isolated from the reaction mixture by ordinary methods, and it can be easily purified from its impurities, byproducts, contaminants, and the like by means of separation, for example, by crystallization or by chromatography.

Chemical Definitions

The term "alkyl" used herein alone or as part of another group refers to any saturated aliphatic hydrocarbon, including straight-chain, and branched-chain. In one embodiment, the alkyl group has 1-6 carbons designated here as $C_{1-6}$-alkyl. In another embodiment, the alkyl group has 1-4 carbons designated here as $C_{1-4}$-alkyl. Examples of alkyl groups include methyl, ethyl, n-propyl, isopropyl, n-butyl, sec-butyl, isobutyl, t-butyl, n-pentyl, 2-pentyl, 3-pentyl, 1-hexyl, 2-hexyl, 3-hexyl and the like. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. Each possibility represents a separate embodiment of the present invention.

The term "aryl" used herein alone or as part of another group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "Hal", "halogen" or "halo" as used herein alone or as part of another group refers to chlorine, bromine, fluorine, and iodine.

The principles of the present invention are demonstrated by means of the following non-limitative examples.

EXAMPLES

Specific compounds which are representative of the present invention were prepared as per the following examples and reaction sequences. No attempt has been made to optimize the yields obtained in any of the reactions.

Unless otherwise noted, the materials used in the examples were obtained from readily available commercial suppliers or synthesized by standard methods known to one skilled in the art of chemical synthesis. The work-up treatment in each step can be applied by a typical method, wherein isolation and purification is performed as necessary by selecting or combining conventional methods, such as crystallization, recrystallization, distillation, partitioning, silica gel chromatography, preparative HPLC and the like.

Starting materials were prepared according to following literature data:

Trans-1,2-(1R,2R)-bis(methanesulfonyloxymethyl)-cyclohexane (EPO464846; JP2006282527)

Enantiomerically pure trans-1,2-cyclohexanedicarboxylic acid monoamide was prepared according to a procedure published for the racemic material by ring-opening the anhydride precursor with dry ammonia gas (P. Arrizabalaga, P. Castan, J.-P. Laurent, *J. Am. Chem. Soc.* 1984, 106, 4814-4818). The product was separated as a white solid. Yield: quantitative, m.p. 197° C.

((1R,2R)-2-(aminomethyl)cyclohexyl)methanol was prepared by reduction of enantiomerically pure trans-1,2-cyclohexanedicarboxylic acid monoamide using sodium borohydride-boron trifluoride etherate.

Benzo[d]isothiazol-3-amine (16) was prepared according to (*Liebigs Ann. Chem.* 1977, 20-26; *Chem. Med. Chem.* 2007, 2, 113-119; *J. Med. Chem.* 2008, 51, 1231-1241 U.S. Pat. No. 4,140,692).

Example 1

Preparation of (3aR,4S,7R,7aS)-2-(((1R,2R)-2-(hydroxymethyl)cyclohexyl) methyl)hexahydro-1H-4,7-methanoisoindole-1,3(2H)-dione (13)

A mixture of bicyclo[2.2.1]heptane-2-exo-3-exo dicarboxylic anhydride (6) (40 mmol), ((1R,2R)-2-(aminomethyl)cyclohexyl)methanol (9) (40.2 mmol) and triethylamine (0.7 mmol) in toluene (500 ml) was heated under reflux for 4-6 hrs with azeotropic removal of water using a Dean-Stark apparatus. The reaction was then concentrated under reduced pressure. Ethyl acetate was added to the residue and the organic phase was washed with 1N HCl solution (20-30 ml) to eliminate the unreacted triethylamine, dried over anhydrous magnesium sulfate and concentrated in vacuum. The compound (13) is pure enough to be used in the next step without any further purification.

Example 2

Preparation of ((1R,2R)-2-(((3aR,4S,7R,7aS)-1,3-dioxohexahydro-1H-4,7-methanoisoindol-2(3H)-yl) methyl)cyclohexyl)methyl methanesulfonate (14, R=Me)

a) To a solution of compound (13) (10 mmol) in pyridine (10 ml), methanesulfonyl chloride (15 mmol) was added dropwise with stirring at 0-4° C. The mixture was stirred at room temperature for 2-3 hr while monitoring by HPLC. After reaction completion, ethyl acetate was added to the reaction mixture and the organic phase was washed with 1N HCl solution (20-30 ml) to eliminate pyridine, dried over anhydrous magnesium sulfate and concentrated in vacuum, to give an oily residue sufficiently pure for the next step.
b) A mixture of trans-1,2-(1R,2R)-bis(methanesulfonyloxymethyl)-cyclohexane (2) (33.3 mmol) and bicyclo[2.2.1]heptane-2-exo-3-exo-dicarboximide (33.3 mmol), potassium carbonate (50 mmol) in 2-propanol (200 ml) was refluxed for 4 hours with intense stirring while monitoring by HPLC. After reaction completion the solvent was concentrated under reduced pressure and water (50 ml) and ethyl acetate (100 ml) were added to the residue. The organic phase was separated and washed with water two more times (2×50 ml), dried over sodium sulfate and concentrated under reduced pressure to give an oily residue sufficiently pure for the next step, with 99% yield. MS: m/z 370 (MH+). NMR spectrum corresponds to structure.

Example 3

Preparation of (3aR,7aR)-2,2-bis(2-hydroxyethyl) octahydro-1H-isoindolium mesylate (7)

A mixture of trans-1,2-(1R,2R)-bis(methanesulfonyloxymethyl)-cyclohexane (2) (10 mmol), diethanolamine (10 mmol), sodium carbonate (15 mmol) in chlorobenzene (40 ml) was refluxed for 20-25 hours. The reaction mixture was concentrated under reduced pressure and acetonitrile (20 ml) was added. The mixture was heated to reflux and filtered while hot, and the filtrate was concentrated to give the (3aR, 7aR)-2,2-bis(2-hydroxyethyl)octahydro-1H-isoindolium mesylate (7) with 99% yield. MS: m/z 214 (M-OMs). NMR spectrum corresponds to structure.

Example 4

Preparation of (3aR,4S,7R,7aS)-2-(((1R,2R)-2-((bis (2-hydroxyethyl)amino)methyl) cyclohexyl)methyl) hexahydro-1H-4,7-methanoisoindole-1,3(2H)-dione (10)

A mixture of the compound (7) (5.0 mmol), bicyclo[2.2.1] heptane-2-exo-3-exodicarboximide (5) (6 mmol), potassium carbonate (7.5 mmol), and dimethylformamide (40 ml) was heated at 120° C. for 16 hours, followed by the removal of the solvent under reduced pressure. Water and ethyl acetate were added to the residue and the organic phase separated. The aqueous phase was extracted twice more with ethyl acetate. The combined organic phases were dried over sodium sulfate and concentrated under reduced pressure to give the desired compound which was sufficiently pure for the next step. (80% yield). MS: m/z 379 (MH+). NMR spectrum corresponds to structure.

Example 5

Preparation of ((((1R,2R)-2-(((3aR,4S,7R,7aS)-1,3-dioxohexahydro-1H-4,7-methanoisoindol-2(3H)-yl) methyl)cyclohexyl)methyl)azanediyl)bis(ethane-2,1-diyl)dimethanesulfonate (12)

Compound (10) (35.0 mmol) was dissolved in triethylamine (100 mmol) and dichloromethane (120 ml), and methanesulfonyl chloride (75 mmol) was added dropwise at 0-5° C. The resulting mixture was stirred at this temperature for 1 hour and allowed to react at room temperature for 3 hours. The reaction mixture was washed with water, dried over sodium sulfate and concentrated. The desired compound (12) was obtained with 50% yield. MS: m/z 536 (MH+). NMR spectrum corresponds to structure.

Example 6

Preparation of (1R,2S,3R,4S)—N-[(1R,2R)-2-[4-(1, 2-Benzisothiazol-3-yl)-1-piperazinylmethyl]-1-cyclohexylmethyl]-2,3-bicyclo[2.2.1]heptanedicarboxyimide (Lurasidone (1) free base)

Benzo[d]isothiazol-3-amine (16) (22.5 mol) was added to a solution of compound (12) (21 mmol) in 200 ml isopropanol. Potassium carbonate (84 mmol) was added to the mixture. The resulting solution was allowed to react while stirring overnight at reflux. Following reaction completion, the mixture was filtered and the solvent was evaporated in vacuum, to give the desired compound as a residue.

Example 7

Preparation of (1R,2S,3R,4S)—N-[(1R,2R)-2-[4-(1, 2-Benzisothiazol-3-yl)-1-piperazinylmethyl]-1-cyclohexylmethyl]-2,3-bicyclo[2.2.1]heptanedicarboxyimide hydrochloride (Lurasidone (1) hydrochloride)

The residue from the previous example was treated with hydrochloric acid in acetone according to U.S. Pat. No. 7,605,260, the contents of which are incorporated by reference herein, to give 85% overall (two stage) yield, m.p. 215-217° C. MS: m/z 493 (MH+) and NMR spectrum corresponds to the desired structure.

Example 8

Preparation of (1R,2S,3R,4S)—N-[(1R,2R)-2-[4-(1, 2-Benzisothiazol-3-yl)-1-piperazinylmethyl]-1-cyclohexylmethyl]-2,3-bicyclo[2.2.1]heptanedicarboxyimide (Lurasidone (1) hydrochloride) from compound (14)

A mixture of compound (14) (0.62 mmol), potassium carbonate (0.94 mmol) and 3-(1-piperazinyl-1,2-benzisothiazole (17) (0.62 mmol) in xylene (6 ml) was refluxed for 40 hrs. The mixture was cooled and water (20 ml) and ethyl acetate (10 ml) were added. The organic phase was separated and extracted with 6N HCl solution (3×7 ml). The acidic phases were combined and extracted with dichloromethane (3×20 ml). The combined organic phases were concentrated to give crude Lurasidone hydrochloride. The residue was purified by trituration with Ethyl acetate, obtaining pure Lurasidone hydrochloride with 55% yield, MS: m/z 493 (MH+). NMR spectrum corresponds to structure m.p. 215-217° C.

Example 9

Preparation of 3-(1-piperazinyl)-1,2-benzisothiazole (17)

3-(Methanesulfonyloxy)-1,2-benzisothiazole (6.0 mmol) [prepared from 2,1-benzisothiazol-3(1H)-one with methanesulfonyl chloride. and pyridine in methylene chloride] and diethanolamine (7.0 mmol) were stirred in dry tetrahydrofuran (25 ml) with triethylamine (8.0 mmol) for 20 hours at room temperature with TLC monitoring. The reaction mixture was diluted with ethyl acetate and washed subsequently with aqueous sodium carbonate, water and brine. The organic layer was dried over magnesium sulfate, filtered, and evaporated in vacuo.

Crude 3-[bis(hydroxyethyl)]amino-1,2-benzisothiazole (6.0 mmol) was dissolved in 20 ml of acetonitrile and triethylamine (18 mmol). Methanesulfonyl chloride (13 mmol) was dropwise added at 0-4° C. The resulting mixture was stirred at this temperature for 1 hour and at room temperature for 3-5 hours. The reaction mixture was washed with water, dried over sodium sulfate and concentrated. The residue was dissolved in methanol-ammonium hydroxide solution and heated to reflux. After 20-24 hours at reflux, the solution was sampled for thin-layer chromatography (elution with methylene chloride/isopropanol/triethylamine, 15:5:1) which showed that the reaction was complete. Half volume of methanol was evaporated under reduced pressure and water (30 mL) was added, following by toluene (50 ml). Then the separated aqueous layer was washed with fresh toluene (10 ml). The combined toluene layers were washed with water (20 ml) and then treated with decolorizing carbon. The mixture was heated to reflux and filtered hot through celite. The celite cake was rinsed with toluene (10 mL), and the combined washing and filtrate were concentrated at reduced pressure to 10 mL. Isopropanol (22 ml) was added to the concentrate and the yellowish solution was cooled to 20° C. The pH of the solution was slowly adjusted to 3.5-4.0 with of concentrated hydrochloric acid. The resulting slurry was cooled to 0-5° C., stirred for 1 hour, and then filtered. The product was washed with cold isopropanol and dried in vacuum at 40° C. for 24 hours. The title compound (4.32 mmol) was isolated as a light yellow solid in 71% yield (>98.5% purity).

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

What is claimed is:

1. A process for the preparation of a compound of formula (1'), or a salt thereof, which comprises:
(a) reacting a compound of formula A' with a compound of formula B' to form a compound of formula C':

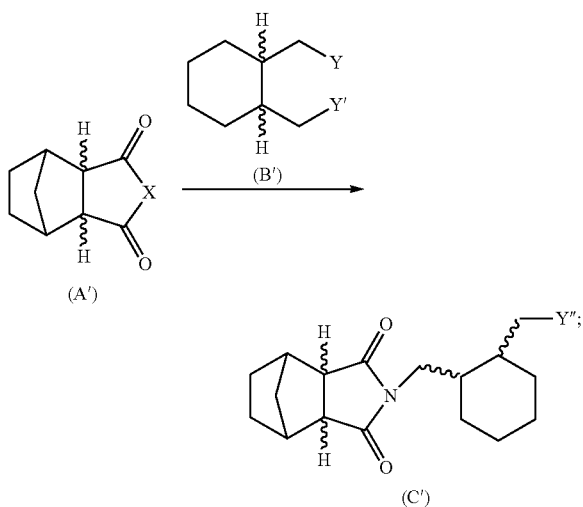

and
(b) reacting a compound of formula C' with a compound of formula D to form a compound of formula 1', or a salt thereof

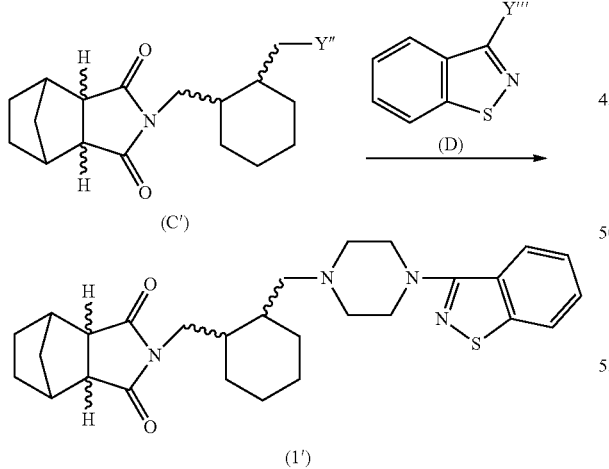

wherein
X is selected from O and NH;
Y and Y' are independently selected from OH, OSO$_2$R, NH$_2$, and Hal, or Y and Y' together are N(CH$_2$CH$_2$Z)$_2$ wherein Z is selected from OH, OSO$_2$R, and Hal;
Y" is selected from OH, OSO$_2$R, NH$_2$, Hal, and N(CH$_2$CH$_2$Z)$_2$;
Y'" is selected from NH$_2$ and piperazinyl;
Hal is selected from Cl, Br, and I; and
R is selected from substituted or unsubstituted alkyl and aryl.

2. The process according to claim 1, wherein the compound of formula (1') is Lurasidone of formula (1), or a pharmaceutically acceptable salt thereof, and the process comprises the steps of:
(a) reacting a compound of formula A with a compound of formula B to form a compound of formula C:

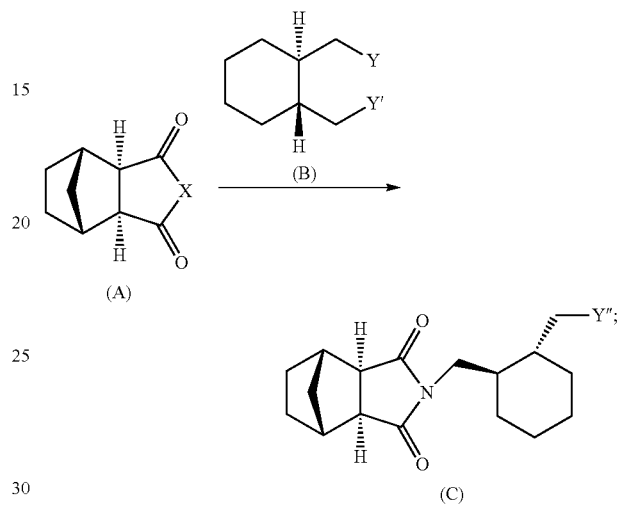

and
(b) reacting a compound of formula C with a compound of formula D to form Lurasidone, or a salt thereof:

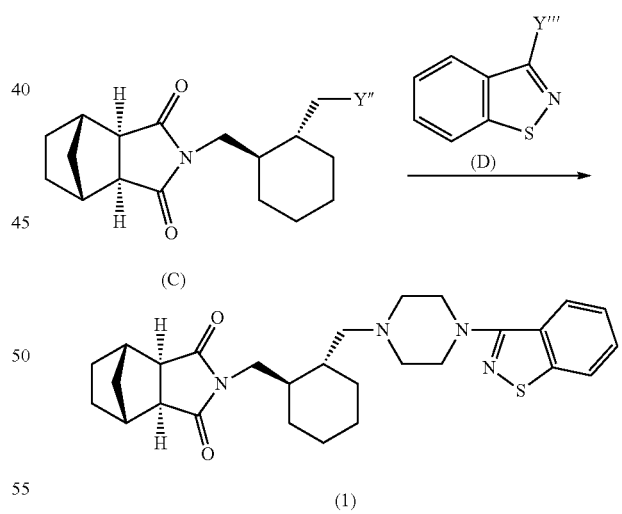

wherein
X, Y, Y', Y", Y'", Hal and R are as defined in claim 1.

3. The process according to claim 1, further comprising the step of converting the compound of formula (1) or (1') to its pharmaceutically acceptable salt.

4. The process according to claim 3, wherein the compound is Lurasidone HCl.

5. The process according to claim 1, wherein X is O; Y and Y' are independently selected from OH and NH$_2$; and Y" is OH.

6. The process according to claim 5, wherein step (a) comprises reacting a compound of formula (9) with a compound of formula (6) to generate a compound of formula (13):

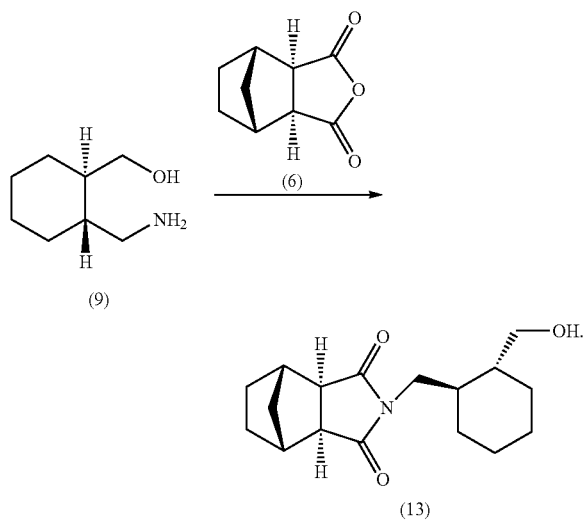

(9)

(6)

(13)

7. The process according to claim 1, wherein X is NH; Y and Y' together are $N(CH_2CH_2OH)_2$ and Y'' is $N(CH_2CH_2OH)_2$.

8. The process according to claim 7, wherein step (a) comprises reacting a compound of formula (7) with a compound of formula (5) to generate a compound of formula (10):

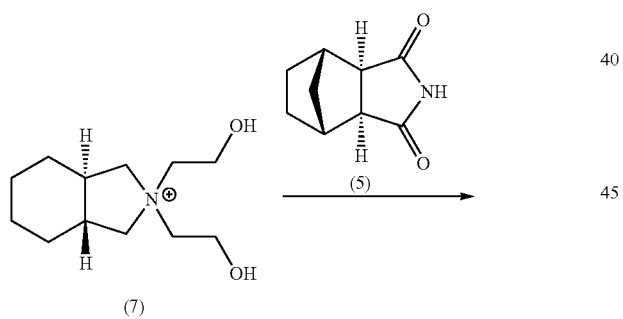

(7)

(5)

(10)

9. The process according to claim 1, wherein Y'' is $N(CH_2CH_2OSO_2R)_2$ or $N(CH_2CH_2Hal)_2$ and Y''' is $NH_2$.

10. The process according to claim 9, wherein step (b) comprises reacting a compound of formula (12) with a compound of formula (16) to generate Lurasidone (1):

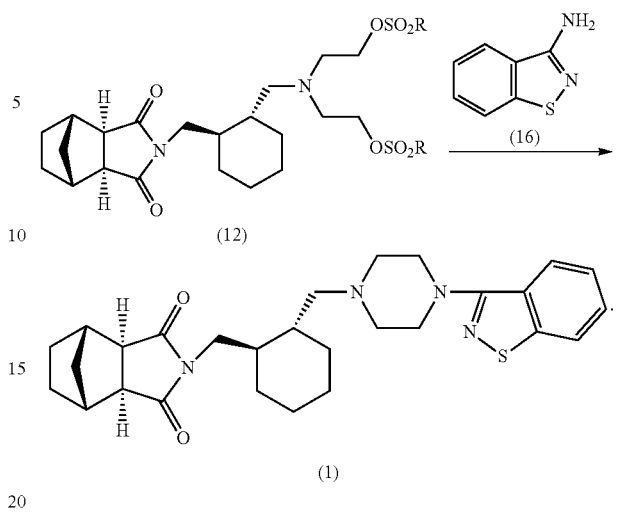

(12)

(16)

(1)

11. The process according to claim 9, wherein step (b) comprises reacting a compound of formula (11) with a compound of formula (16) to generate Lurasidone (1):

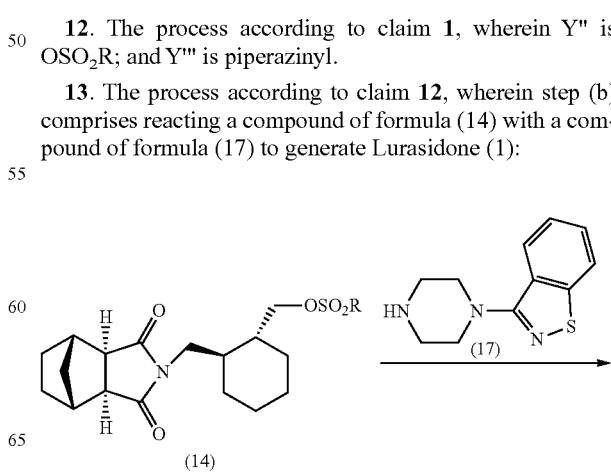

(11)

(16)

(1)

12. The process according to claim 1, wherein Y'' is $OSO_2R$; and Y''' is piperazinyl.

13. The process according to claim 12, wherein step (b) comprises reacting a compound of formula (14) with a compound of formula (17) to generate Lurasidone (1):

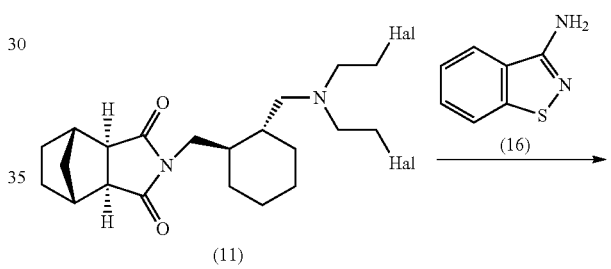

(14)

(17)

-continued
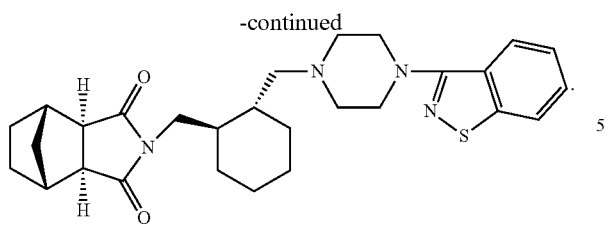
(1)
* * * * *